(12) United States Patent
Seals et al.

(10) Patent No.: US 10,307,437 B2
(45) Date of Patent: Jun. 4, 2019

(54) METHODS FOR TREATMENT OF VASCULAR ENDOTHELIAL DYSFUNCTION USING NICOTINAMIDE MONONUCLEOTIDE

(71) Applicant: The Regents of the University of Colorado, a Body Corporate, Denver, CO (US)

(72) Inventors: Douglas R. Seals, Boulder, CO (US); Lindsey Gano, Denver, CO (US); Natalie Poliektor, Denver, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 178 days.

(21) Appl. No.: 15/126,548

(22) PCT Filed: Mar. 24, 2015

(86) PCT No.: PCT/US2015/022267
§ 371 (c)(1),
(2) Date: Sep. 15, 2016

(87) PCT Pub. No.: WO2015/148522
PCT Pub. Date: Oct. 1, 2015

(65) Prior Publication Data
US 2017/0087171 A1    Mar. 30, 2017

Related U.S. Application Data

(60) Provisional application No. 61/969,658, filed on Mar. 24, 2014.

(51) Int. Cl.
*A61K 31/706* (2006.01)

(52) U.S. Cl.
CPC .................. *A61K 31/706* (2013.01)

(58) Field of Classification Search
CPC .... A61K 31/406; A61K 31/455; A61K 45/06; A61K 31/706
See application file for complete search history.

(56) References Cited

U.S. PATENT DOCUMENTS

| | | | |
|---|---|---|---|
| 2007/0082373 A1* | 4/2007 | Imai | A61K 31/455 435/14 |
| 2009/0030071 A1 | 1/2009 | Shaw et al. | |
| 2012/0328526 A1 | 12/2012 | Kristian | |

FOREIGN PATENT DOCUMENTS

| | | |
|---|---|---|
| WO | WO2009142731 | 11/2009 |
| WO | WO2013002879 | 1/2013 |
| WO | WO2015148522 | 10/2015 |

OTHER PUBLICATIONS

Sena (Biochimica et Biophysica Acta; 2013, 1832, 2216-2231).*
EPO; Extended European Search Report issued in Application No. 15768836.7 (dated Aug. 29, 2017).
Chung et al; "Regulation of SIRT1 in cellular functions: Role of polyphenols", Archives of Biochemistry and Biophysics, Academic Press, US, vol. 501, No. 1, pp. 79-90, (Sep. 1, 2010).
Imai et al; "A possibility of nutriceuticals as an anti-aging intervention: Activation of sirtuins by promoting mammalian NAD biosynthesis", Pharmacological Research, Academic Press, London, GB, vol. 62, No. 1, pp. 42-47 (Jul. 1, 2010).
Picclotto et al., "Nicotinamide mononucleotide supplementation reverses vascular endothelial dysfunction and large elastic artery stiffness in old mice", FASEB Journal, vol. 28, No. 1, Supplement 698.10 (Apr. 2014).
International Search Report and Written Opinion issued in PCT/US2015/022267 dated Jun. 17, 2015.
Hein et al., "Acute Retinal Ischemia Inhibits Endothelium-Dependent Nitric Oxide Mediated Dilation of Retinal Arterioles via Enhanced Superoxide Production", Investigative Ophthalmology & Visual Science, Jan. 2012, vol. 53, No. 1, pp. 30-36.
Mattagajasingh et al., "SIRT1 promotes endothelium-dependent vascular relaxation by activating endothelial nitric oxide synthase", Proceedings of the National Academy of Sciences of the United States of America (PNAS), Sep. 11, 2007, vol. 104(37), pp. 14855-14860.
Borradaile et al., "Nicotinamide phosphoribosyltransferase imparts human endothelial cells with extended replicative lifespan and enhanced angiogenic capacity in a high glucose environment", Aging Cell, Mar. 13, 2009, vol. 8(2), pp. 100-112.

* cited by examiner

*Primary Examiner* — Pancham Bakshi
(74) *Attorney, Agent, or Firm* — David P. Halstead; Foley Hoag LLP

(57) ABSTRACT

This invention is about the compositions and methods for assessing and treating vascular endothelial dysfunction. Various aspects provide a method for treatment of vascular endothelial dysfunction, comprising administering a composition comprising nicotinamide mononucleotide and a pharmaceutical excipient to a subject. In one embodiment the dose is administered to subjects in response to the indicator. In another embodiment the dose is administered chronically to subjects.

21 Claims, 7 Drawing Sheets

METHODS FOR TREATMENT OF VASCULAR ENDOTHELIAL DYSFUNCTION USING NICOTINAMIDE MONONUCLEOTIDE

CROSS REFERENCE TO RELATED APPLICATIONS

This application is a U.S. National Stage patent application that claims priority to, and the benefit of, PCT Patent Application PCT/US 15/22267, filed on Mar. 24, 2015, entitled "METHODS FOR TREATMENT OF VASCULAR ENDOTHELIAL DYSFUNCTION USING NICOTINAMIDE MONONUCLEOTIDE," which claims priority to U.S. Provisional Patent Application Ser. No. 61/969,658, filed Mar. 24, 2014, entitled "METHODS FOR TREATMENT OF VASCULAR ENDOTHELIAL DYSFUNCTION USING NICOTINAMIDE MONONUCLEOTIDE," which are incorporated herein by reference in their entireties.

GOVERNMENT RIGHTS

This invention was made with government support under grant numbers R37 AG013038 and AG000279 awarded by the National Institutes of Health. The government has certain rights in the invention.

FIELD OF INVENTION

The present disclosure relates, generally, to compositions and methods for the treatment of vascular endothelial dysfunction using compositions comprising nicotinamide mononucleotide.

BACKGROUND OF THE INVENTION

Cardiovascular diseases (CVD) remain the leading cause of death in modern society in developed nations. The number of older adults in the developed world is expected to at least double by 2050, and this is associated with projections of marked increases in CVD burden.

Aging increases the risk of CVD largely due to the dysfunction of the arteries, namely endothelial dysfunction and large elastic artery stiffness. Vascular endothelial dysfunction is primarily assessed via endothelium-dependent dilation (EDD) and is impaired largely due to increased superoxide ($O_2^-$) production. Increased $O_2^-$ reduces the bioavailability of the potent vasodilator and vasoprotective molecule nitric oxide (NO). Increased aortic stiffness, in particular, reduces the ability to buffer increases in pressure produced by systolic ejection of blood into the large elastic arteries with each cardiac contraction. This increases systolic blood pressure and arterial pulse pressure (the difference between systolic and diastolic blood pressure), as well as the "pulsatility" of blood flow, which is transmitted to the microvasculature of vulnerable high-flow organs such as the brain and kidney, causing end-organ damage and other pathophysiological effects. Similarly, increased arterial stiffness has been linked to endothelial dysfunction and is now recognized as the major independent risk factor for age-associated CVD. Therefore, there is an urgent need to develop treatments that reduce the risk of CVD with aging.

Without being bound by theory, the mechanisms by which arteries stiffen with age are not completely understood, but are thought to include changes in the composition of structural proteins within the arterial wall. Collagen (type I) is the primary load-bearing protein in the arterial wall, and its abundance is increased with advancing age. In contrast, elastin, the main structural protein conferring elasticity, is reduced in old arteries. It has previously been shown in mice (Fleenor B. S. et al. 2012a, Aging Cell. 11, 269-276) and cultured aortic fibroblasts (Fleenor B. S. et al. 2010, J Physiol. 588, 3971-3982) that oxidative stress contributes to some or all of the age-associated structural changes seen within the arteries.

Two key antecedents and independent predictors of clinical CVD in older adults are thought to include vascular endothelial dysfunction, assessed by endothelium-dependent dilation (EDD), and large elastic artery stiffness, measured by aortic pulse wave velocity (aPWV). A common mechanism that contributes to both vascular endothelial dysfunction and large elastic artery stiffness with aging is believed to involve excessive superoxide-associated vascular oxidative stress (Seals D. R. et al. 2011, Clin Sci 120, 357-375; Fleenor B. S. et al. 2012a, Aging Cell. 11, 269-276; Bachschmid M. M. et al. 2013, Ann Med. 45, 17-36). Increased vascular production of superoxide occurs with aging and reduces the bioavailability of the vasoprotective and vasodilatory molecule nitric oxide (NO), while also causing alterations in major structural proteins (collagen and elastin) in the large elastic arteries (i.e., the aorta and carotid arteries). These changes contribute directly to age-related endothelial dysfunction and increased arterial stiffness. As such, treatments that reduce the excessive superoxide production in aging arteries hold the potential for improving age-associated vascular dysfunction.

It is recognized that there is an association between endothelial dysfunction and a decline in cognitive and motor (physical) function during both normal aging and in age-associated disease states. It is further recognized that endothelial function plays a role in the systemic regulation of metabolism, blood fluidity, tissue perfusion, immune function and enhancement of longevity.

It has been previously shown that lifelong caloric restriction (CR), as well as short-term CR in old animals, prevents or reverses endothelial dysfunction and large elastic artery stiffening by reducing superoxide production, increasing NO bioavailability and modifying structural proteins (Rippe C. et al. 2010 Aging Cell. 9, 304-312; Donato A. J. et al. 2013, Aging Cell. 12, 772-783). However, because adherence to CR is not practical for most humans, there is growing interest in pharmacological therapies that may induce the benefits of CR.

Sirtuins are a class of enzyme proteins that possess deacylase activity, including deacetylase, desuccinylase, demalonylase, demyristoylase and depalmitoylase activity, some of the sirtuins (for example, SIRT6) also possess mono-ribosyltransferase activity. The expression and activity of sirtuin enzymes is reduced with advancing age. There are 7 mammalian sirtuins (SIRT 1-7) that correspond to the yeast Sir2 (silent mating-type information regulation). Sirtuins also possess nicotinamide adenine dinucleotide ($NAD^+$)-dependent deacetylase activity. Mammalian SIRT1, one of seven members in the sirtuin family of protein deacetylases/deacylases, is a nicotinamide adenine dinucleotide ($NAD^+$)-dependent deacetylase that acts as a metabolic energy sensor implicated in several of the beneficial effects of CR, including reduced oxidative stress (Boily G. et al. 2008, PLoS One. 3, e1759; Merksamer P. I. et al. 2013, Aging (Albany N.Y.). 5, 144-150). Enhancing $NAD^+$ biosynthesis with $NAD^+$ precursors, such as NMN and nicotinamide riboside (NR), increases the activity of the $NAD^+$-dependent deacetylase SIRT1 (Imai S. 2010, Pharmacol Res.

62, 42-47; Satoh A. et al. 2011, Handb Exp Pharmacol. 206, 125-162; Canto C. et al. 2012, Cell Metab. 15, 838-847).

With advancing age, there is a reduction of the expression and activity of sirtuins in mammals and humans. Because of this, sirtuins are believed to influence many aging processes. SIRT1 expression in endothelial cells is positively associated with EDD in young and older adults (Donato A. J. et al., 2011 J. Physiol. 589, 4545-4554), implying that SIRT1 may influence vascular function in humans. Previous studies show that reduced SIRT1 expression and activity is a key mechanism mediating impaired EDD in aging arteries (Rippe C. et al. 2010, Aging Cell. 9, 304-312; Donato A. J. et al. 2011, J Physiol. 589, 4545-4554; Gano L. B. et al. 2014, Am J Physiol Heart Circ Physiol. 307, H1754-1763), and recent findings indicate that pharmacological activation of SIRT1 with the compound SRT1720 improves EDD in old mice in part by reducing oxidative stress (Gano L. B. et al. 2014, Am J Physiol Heart Circ Physiol. 307, H1754-1763). Oxidative stress has been shown to play an important role in the development of vascular endothelial dysfunction and large elastic artery stiffness associated with increasing age (Lakatta E. G. & Levy, 2003 Heart Fail Rev. 7, 29-49; Seals et al. 2011, Clin Sci 120, 357-375). Oxidative stress in the vasculature leads to a decrease in NO bioavailability, thus causing endothelial dysfunction and stiffening of the large elastic arteries. Superoxide reacts with NO, forming peroxynitrite ($ONOO^-$), which reduces the bioavailability of NO; this results in less bioavailable NO to contribute to vasodilation. Furthermore, $ONOO^-$ oxidizes tyrosine residues on proteins post-translationally producing nitrotyrosine, one key marker of oxidative stress.

It has been established that oxidative stress and inflammation are intimately connected (Csiszar A. et al. 2008, J Appl Physiol. 105, 1333-1341; Ungvari Z. et al. 2010, J Gerontol A Biol Sci Med Sci. 65, 1028-1041) and SIRT1 has been found to modulate the activity of nuclear factor kappa B (NFκB) and tumor necrosis factor alpha (TNFα) (Yoshino J et al., 2011, Cell Metab. 14, 528-536), both of which are master regulators of the inflammatory process. The p65 subunit of NFκB is a major target of SIRT1, and is deacetylated in response to SIRT1 activation.

$NAD^+$ bioavailability also decreases with age in various mammalian tissues, and restoring $NAD^+$ levels has been shown to ameliorate high-fat diet- and age-induced Type 2 Diabetes in mice while restoring gene expression related to oxidative stress and inflammation to that of a healthy, non-diabetic mouse, partly through SIRT1 activation.

SUMMARY OF THE INVENTION

Compositions and methods for assessing and treating vascular endothelial dysfunction are described herein. In various aspects, methods of treating vascular endothelial dysfunction are provided. In various embodiments, the method comprises determining an indicator of vascular endothelial dysfunction in a subject. In further embodiments, the method comprises administering a daily dose of a composition comprising nicotinamide mononucleotide and a pharmaceutical excipient. In further embodiments, the dose of nicotinamide mononucleotide is from about 1 mg to about 25 mg per kg body weight per day. In further embodiments, the dose is from about 18 mg of nicotinamide mononucleotide per kg body weight per day. In further embodiments, the dose is administered chronically to subjects. In further embodiments, the dose is administered to subjects in response to the indicator.

In further embodiments, the methods comprise determining a subsequent effect on vascular endothelial dysfunction in the subject. In further embodiments, the indicator of vascular endothelial dysfunction comprises determining the extent of endothelium-dependent dilation and/or artery stiffness in a subject. In further embodiments, the extent of endothelium-dependent dilation is associated with increased superoxide production. In further embodiments, the extent of endothelium-dependent dilation is associated with decreased SIRT1 expression. In further embodiments, the extent of endothelium-dependent dilation and/or artery stiffness is decreased in response to administration of the composition comprising nicotinamide mononucleotide. In further embodiments, the decrease in the extent of endothelium-dependent dilation further comprises a decrease in superoxide production and an increase in nitric oxide bioavailability. In further embodiments, the decrease in the extent of endothelium-dependent dilation further comprises an increase in SIRT1 protein expression and activity. In further embodiments, the composition is administered over a period of time of about 30 days, about 3 months, about 6 months, about 12 months, about 18 months, about 2 years, about 5 years, about 7 years, about 10 years, about 15 years, about 20 years, about 25 years, about 30 years, about 35 years, about 40 years, or continued therapy over the lifetime of the subject.

In various aspects of the invention, NMN treatment selectively reduces stiffness in old animals. In further aspects, the methods of decreasing endothelium-dependent dilation and/or arterial stiffness in a subject, comprise determining the extent of endothelium-dependent dilation and/or arterial stiffness in a subject and administering a daily dose of a composition comprising nicotinamide mononucleotide and a pharmaceutical excipient wherein the composition comprises from about 1 mg to about 25 mg per kg body weight per day. In further embodiments, the dose is from about 18 mg of nicotinamide mononucleotide per kg body weight per day. In further embodiments, the dose is administered chronically to said subject. In further embodiments, a decrease in endothelium-dependent dilation and/or arterial stiffness is associated with an increase in bioavailability of nicotinamide adenine dinucleotide ($NAD^+$). In further embodiments, a decrease in endothelium-dependent dilation and/or arterial stiffness further comprises a decrease in superoxide production, an increase in bioavailability of nitric oxide, and/or an increase in SIRT1 protein expression and activity.

In aspects of the invention, NMN treatment activates SIRT1 and reduces inflammation and oxidative stress, resulting in improved vascular function.

In aspects of the invention, treatment with NMN reverses age-associated vascular dysfunction by improving endothelial function and reducing large elastic artery stiffness in old C57Bl/6 mice, while restoring the age-related decline in SIRT1 protein expression and reducing oxidative stress. In aspects of the invention, treatment with NMN selectively restores the activity of SIRT1 in the arteries of old mice to that of young controls. In further aspects, the ratio of acetylated to total p65 subunit of the transcription factor NFκB is decreased with NMN treatment.

In aspects of the invention, NMN reverses large elastic artery stiffening associated with aging. In another aspect, NMN treatment normalizes collagen. In a further aspect, NMN treatment partially preserves elastin in the arterial wall.

Further aspects and embodiments will become apparent from the detailed description provided herein. It should be understood that the description and specific examples are intended for purposes of illustration only and are not intended to limit the scope of the present invention.

BRIEF DESCRIPTION OF THE DRAWINGS

The subject matter of the present invention is particularly pointed out and distinctly claimed in the concluding portion of the specification. A more complete understanding of the present invention, however, is best obtained by referring to the detailed description and claims when considered in connection with the drawing figures, wherein like numerals denote like elements and wherein:

DETAILED DESCRIPTION

Figure 1A:
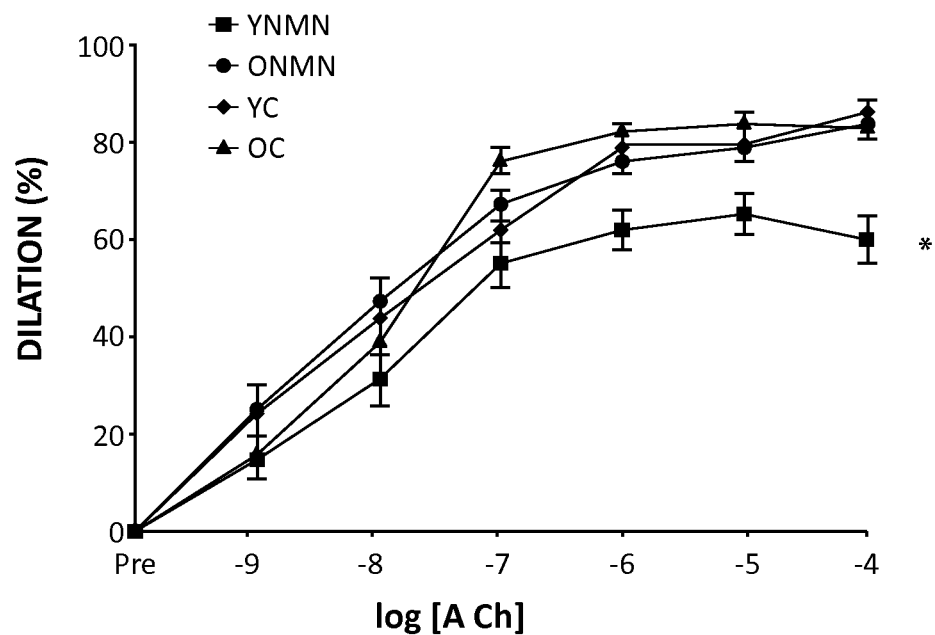
FIG. 1 illustrates dose-responses to the endothelium-dependent dilator acetylcholine (ACh) in young and old control (YC and OC) (FIG. 1A); dose responses to young and old NMN-treated (YNMN and ONMN) mice NO-dependent dilation (FIG. 1B); and the endothelium-independent dilator sodium nitroprusside (SNP) (FIG. 1C).

The following description is merely exemplary in nature and is not intended to limit the present invention, its applications, or its uses. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features.

Furthermore, the detailed description of various embodiments herein makes reference to the accompanying drawing figures, which show various embodiments by way of illustration. While the embodiments are described in sufficient detail to enable those skilled in the art to practice the invention, it should be understood that other embodiments may be realized and that logical and mechanical changes may be made without departing from the spirit and scope of the present invention. Thus, the detailed description herein is presented for purposes of illustration only and not of limitation. For example, steps or functions recited in descriptions of any method, system, or process, may be executed in any order and are not limited to the order presented. Moreover, any of the step or functions thereof may be outsourced to or performed by one or more third parties. Furthermore, any reference to singular includes plural embodiments, and any reference to more than one component may include a singular embodiment.

As used herein, a "pharmaceutically acceptable excipient" refers to any and all solvents, dispersion media, coatings, antibacterial and antifungal agents, isotonic and absorption delaying agents, and the like that are physiologically compatible. Some examples of pharmaceutically acceptable excipients include water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable excipients include wetting agents or minor amounts of auxiliary substances such as wetting or emulsifying agents, preservatives or buffers, which enhance the shelf life or effectiveness of the composition. Pharmaceutical compositions of the present invention and methods for their preparation will be readily apparent to those skilled in the art. Such compositions and methods for their preparation may be found, for example, in *Remington's Pharmaceutical Sciences*, 19th Edition (Mack Publishing Company, 1995). Pharmaceutical compositions are preferably manufactured under GMP conditions. A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. In some embodiments, one or more active ingredients may be present in the composition in addition to nicotinamide mononucleotide (NMN). The amount of the active ingredient is generally equal to the dosage of the active ingredient which would be administered to a subject or a convenient fraction of such a dosage such as, for example, one-half or one-third of such a dosage.

As used herein, a "therapeutically effective amount" or "effective amount" of a composition refers to an amount effective in the prevention or treatment of a disorder for the treatment of which the composition is effective. A "disorder" refers to any condition that would benefit from treatment with the composition. In some embodiments, a composition of the invention is effective in the treatment of cardiovascular disease. In further embodiments, a composition of the invention is effective in the treatment of vascular endothelial dysfunction.

As used herein, "treated," "treating" or "treatment" refers to the diminishment or alleviation of at least one symptom associated or caused by the state, disorder or disease being treated. For example, treatment can be diminishment of one or more symptoms of a disorder or complete eradication of a disorder.

As used herein, "conditions," "diseases" and "disorders" refers to and includes aging, cardiovascular disease (CVD), atherosclerosis and endothelial dysfunction. In embodiments, the disorder may be a disorder associated with aging, cardiovascular disease, atherosclerosis or endothelial dysfunction, for example cognitive impairments, Alzheimer's Disease, motor dysfunction, insulin resistance and sarcopenia.

In various aspects, without being bound to any theory, $NAD^+$ levels are increased in old C57Bl/6 mice by administering the direct intracellular precursor, nicotinamide mononucleotide (NMN), to increase sirtuin activity, decrease oxidative stress and restore NO bioavailability.

In various aspects of the invention, nicotinamide mononucleotide (NMN) may be administered as an active ingredient in therapeutic compositions, for treating vascular endothelial dysfunction, among others. Generally, NMN is suitable to be administered in association with one or more pharmaceutically acceptable excipient(s). The term 'excipient' is used herein to describe any ingredient other than the active ingredient. The choice of excipient(s) will to a large extent depend on factors such as the particular mode of administration, the effect of the excipient on solubility and stability, and the nature of the dosage form.

Actual dosage levels of the active ingredient(s) (for example, NMN) in pharmaceutical compositions and formulations may be varied so as to obtain an amount of the active ingredient that is effective to achieve the desired therapeutic response for a particular patient, composition, and mode of administration, without being toxic to the patient.

Without being bound to any theory, decreased $NAD^+$ bioavailability is believed to contribute to age-associated vascular dysfunction. In various aspects, NMN may be administered to a subject in a therapeutically effective amount. In further aspects, endothelial function may be assessed via endothelium-dependent dilation (EDD), and aortic stiffness. Endothelial function may be assessed pre- and post-treatment with NMN.

The selected dosage level will depend upon a variety of factors including the activity of the composition found in the formulation, the route of administration, the time of administration, the rate of excretion of the particular composition being employed, the duration of the treatment, other drugs, compounds and/or materials used in combination with the particular composition employed, the age, sex, weight, condition, general health and prior medical history of the patient being treated, and like factors well known in the medical arts.

A physician having ordinary skill in the art can readily determine and prescribe the effective amount of the pharmaceutical composition of the present invention required. For example, the physician could start doses of the composition of the invention employed in the pharmaceutical formulation at levels lower than that required in order to achieve the desired therapeutic effect and gradually increase the dosage until the desired effect is achieved.

In various embodiments, the concentration of the active ingredient is between about 10 mg to about 6000 mg of nictotinamide mononucleotide per ml of liquid formulation. In embodiments, the concentration of NMN is from about 100 mg, about 125 mg, about 150 mg, about 200 mg, about 250 mg, about 300 mg, about 500 mg, about 750 mg, about 1000 mg, about 1200 mg, about 1500 mg, about 2000 mg, about 2500 mg, about 3000 mg, about 3500 mg, about 4000 mg, about 4500 mg, about 5000 mg, about 5500 mg, or about 6000 mg per ml of liquid formulation. In embodiments, the concentration of NMN may be calculated based on a subject's body weight. In embodiments, the concentration of NMN is between about 0.1 mg to about 50 mg per kg body weight. In embodiments, the concentration of NMN is from about 0.1 mg to about 25 mg per kg body weight. In embodiments, the concentration of NMN is from about 1 mg, about 2.5 mg, about 5 mg, about 7.5 mg, about 10 mg, about 12.5 mg, about 15 mg, about 18 mg, about 20 mg, about 22.5 mg, or about 25 mg per kg body weight. In embodiments, the concentration of NMN is from about 1 mg to about 25 mg per kg body weight. In embodiments, the concentration of NMN is from about 18 mg of nicotinamide mononucleotide per kg body weight per day. In embodiments, the concentration of NMN administered to a subject is from about 1,200 mg/day for a subject weighing about 150 lbs.

In various embodiments, a composition of the invention may be administered as a daily dose over a period of time to a subject. In embodiments, a composition of the invention may be administered chronically or long-term. In embodiments, the composition may be administered for a period of days, weeks, months, years or continued therapy over the lifetime of a subject. In embodiments, the composition may be administered for a period of about 30 days, about 3 months, about 6 months, about 12 months, about 18 months, about 2 years, about 5 years, about 7 years, about 10 years, about 15 years, about 20 years, about 25 years, about 30 years, about 35 years, or about 40 years. In embodiments, a treatment regime may be determined for an individual subject dependent on various factors. In some embodiments, a factor may include, but not be limited to, a determination of the change in the extent of endothelial-dependent dilation and/or arterial stiffness in response to administration of the composition of the invention. In further embodiments, stiffening of the large elastic arteries with advancing age can lead to an increase in arterial systolic and pulse pressures, left ventricular hypertrophy, and tissue damage to high-flow vital organs, such as the brain and kidneys. In embodiments, a subject exhibiting an immediate response to the composition, for example, an immediate reduction in endothelial-dependent dilation and/or arterial stiffness, may require less frequent doses than a subject exhibiting a response to the composition at a later time or after several doses.

Any method for administering pharmaceutical or nutriceutical-like compounds in the art may suitably be employed in accordance with the invention.

Example

Supplementation of nicotinamide mononucleotide (NMN), a key $NAD^+$ intermediate, as potentially activating the mammalian $NAD^+$-dependent deacetylase SIRT1 and reverses age-associated vascular dysfunction and oxidative stress was tested. Old control mice (OC) had impaired carotid artery endothelium-dependent dilation (EDD) (60±5 vs. 84±2%), a measure of endothelial function, and nitric oxide (NO)-mediated EDD (37±4 vs. 66±6%), compared with young mice (YC). This age-associated impairment in EDD was restored in OC by the superoxide ($O_2^-$) scavenger TEMPOL (4-hydroxy-2,2,6,6-tetramethylpiperidin-1-oxyl; 82±7%). OC also had increased aortic pulse wave velocity (aPWV, 464±31 vs. 337±3 cm/s) and elastic modulus (EM, 6407±876 vs. 3119±471 kPa), measures of large elastic artery stiffness, compared to YC. OC had greater aortic $O_2^-$ production (2.0±0.1 vs. 1.0±0.1 AU), nitrotyrosine abundance (a marker of oxidative stress), and collagen-I, and reduced elastin and vascular SIRT1 activity, measured by the acetylation status of the p65 subunit of NFκB, compared to YC. Treatment with NMN in old mice restored EDD (86±2%) and NO-mediated EDD (61±5%), reduced aPWV (359±14 cm/s) and EM (3694±315 kPa), normalized $O_2^-$ production (0.9±0.1 AU), decreased nitrotyrosine, reversed collagen-I, partially increased elastin, and restored vascular SIRT1 activity. NMN treatment restores SIRT1 activity and reverses age-related arterial dysfunction and reduces oxidative stress.

Materials and Methods

Animals.

Young (4-8 months) C57Bl/6 male mice were purchased from Charles River and old (26-28 months) C57Bl/6 male mice were obtained from the National Institute on Aging rodent colony. Mice were fed normal rodent chow ad libitum for the duration of the study. After an acclimation period of 2 weeks, the young and old mice were divided into two subgroups: control animals (YC, OC) continued on normal drinking water and the other animals (YNMN, ONMN) received nicotinamide mononucleotide (NMN; Sigma-Aldrich Corp., St. Louis, Mo., USA) supplementation in the drinking water (240 mg/kg/day) for 8 weeks. All mice were housed in an animal care facility at the University of Colorado Boulder on a 12:12 hour light-dark cycle. All animal procedures conformed to the Guide to the Care and Use of Laboratory Animals (NIH publication No. 85-23, revised 1996) and were approved by the UCB Animal Care and Use Committee.

Ex Vivo Carotid Artery Vasodilatory Responses.

EDD and endothelium-independent dilation were determined ex vivo in isolated carotid arteries as previously described (Rippe C. et al. 2010, Aging Cell. 9, 304-312; Sindler A. L. et al. 2011, Aging Cell. 10, 429-437). Mice were anesthetized using isoflurane and euthanized by exsanguination via cardiac puncture. The carotid arteries were carefully excised, cannulated onto glass micropipette tips, and secured with nylon (11-0) sutures in individual myograph chambers (DMT Inc., Ann Arbor, Mich., USA) containing buffered physiological saline solutions. The arteries were pressurized to 50 mmHg at 37° C. and were allowed to equilibrate for 45 minutes before experimentation. After submaximal preconstriction with phenylephrine (2 µM), increases in luminal diameter in response to acetylcholine (ACh: $1\times10^{-9}$-$1\times10^{-4}$ M; Sigma-Aldrich Corp.) with and without co-administration of the NO synthase inhibitor, L-NAME, 0.1 mM, 30 minute incubation; (Sigma-Aldrich Corp.) or the superoxide dismutase mimetic 4-Hydroxy-2,2,6,6-tetramethylpiperidine-1-oxyl (TEMPOL, 0.1 mM, 1 hour incubation; Sigma-Aldrich Corp.) were determined. Endothelium-independent dilation was determined by vasodilation in response to the NO donor sodium nitroprusside (SNP: $1\times10^{-19}$-$1\times10^{-4}$ M; Sigma-Aldrich Corp.).

Figure 1B:
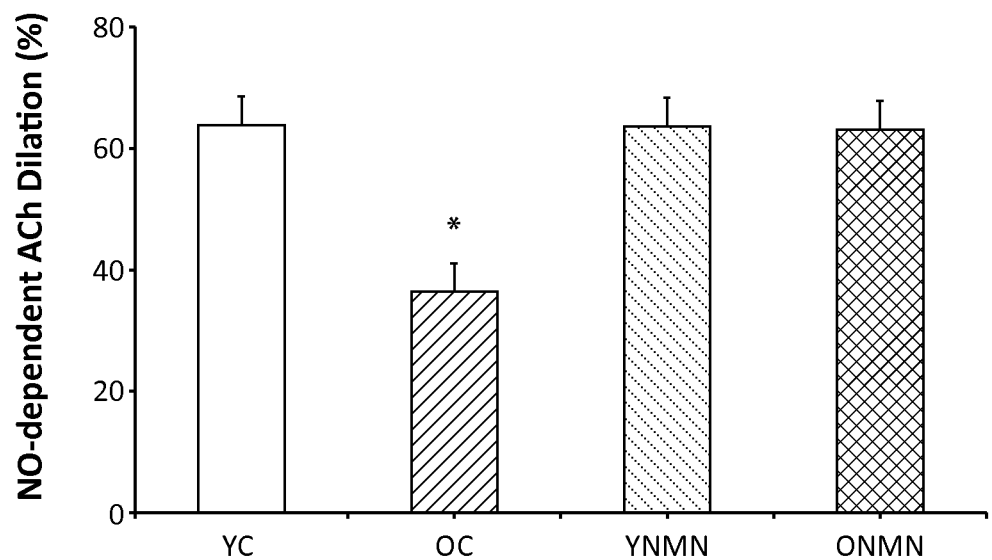
Figure 1C:
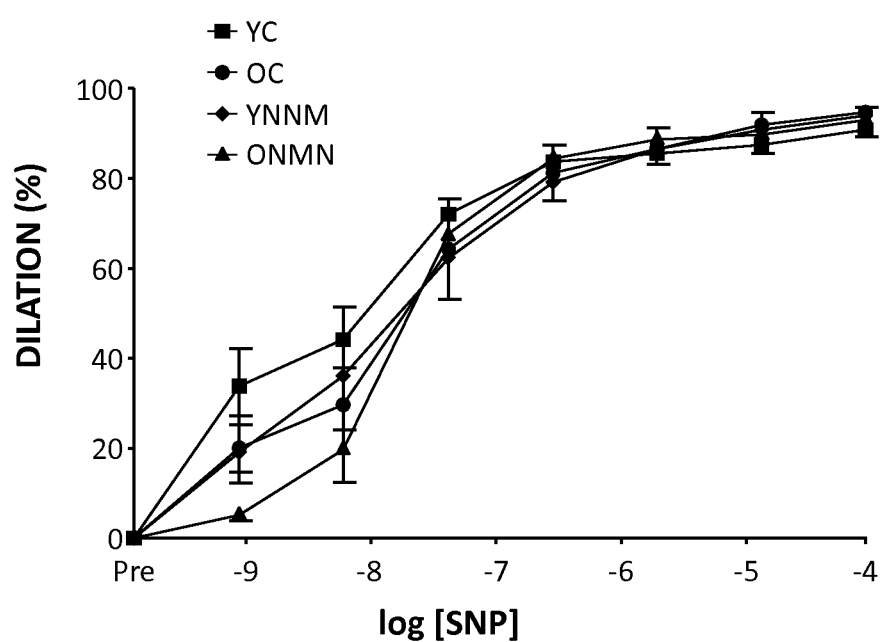
Figure 2A:
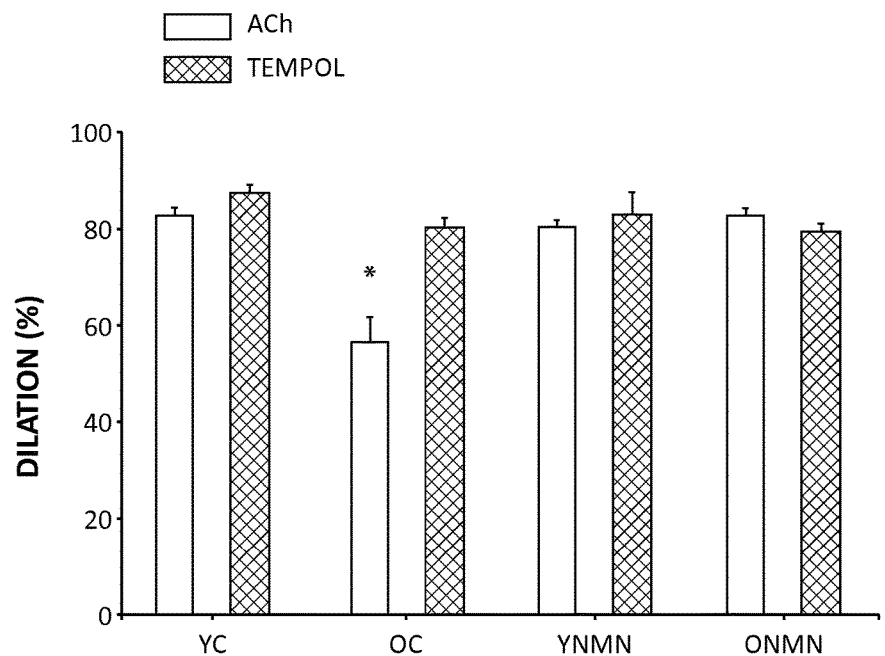
FIG. 2 illustrates maximal dose-response to the endothelium-dependent dilator acetylcholine (ACh) in young and old control (YC and OC) and young and old NMN-treated (YNMN and ONMN) mice in the presence or absence of TEMPOL (FIG. 2A); superoxide production assessed by electron paramagnetic resonance (EPR) (FIG. 2B); and nitrotyrosine (NT) abundance in aorta (FIG. 2C).

All dose-response data are presented as percent dilation, i.e. FIGS. 1A, 1C and 2A. Preconstriction was calculated as a percentage of maximal intra-luminal diameter according to the following formula:

Preconstriction (%)=$(D_m-D_b)/D_m\times100$

Because of differences in maximal carotid artery diameter between young and old animals, vasodilator responses were recorded as actual diameters expressed as a percentage of maximal response according to the following formula:

Dilation (%)=$(D_s-D_b)/(D_m-D_b)\times100$

Where $D_m$ is maximal intra-luminal diameter at 50 mmHg, $D_b$ is the steady-state intra-luminal diameter following preconstriction before the first addition of a drug, and $D_s$ is the steady-state intra-luminal diameter recorded after the addition of a drug.

NO-dependent dilation was determined from maximal EDD (i.e., dilation with the highest dose [$1\times10^{-4}$ M] ACh) in the absence or presence of L-NAME according to the following formula:

NO-dependent dilation (%)=Maximum dilation$_{ACh}$−Maximal dilation$_{ACh+L-NAME}$ In Vivo Aortic Pulse Wave Velocity.

Aortic pulse wave velocity (aPWV) was measured as described previously (Sindler A. L. et al. 2011, Aging Cell. 10, 429-437; Fleenor B. S. et al. 2012b, Exp Gerontol. 47, 588-594). Briefly, mice were anesthetized with 2% isoflurane and placed supine on a heating board with legs secured to electrocardiogram (ECG) electrodes. Aortic blood flow velocity was measured with two Doppler probes placed at the transverse aortic arch and abdominal aorta, respectively. Pre-ejection time, the time between the R-wave of the ECG to foot of the Doppler signal, was determined for each site. aPWV was calculated by dividing the distance between the transverse and abdominal probes by the difference in the thoracic and abdominal pre-ejection times.

In Vitro Elastic Modulus.

In vitro intrinsic mechanical properties of the thoracic aorta were determined and used to calculate the elastic modulus as previously described. Aortic segments (~1.5 mm in length) from mice were cleaned of perivascular fat and other surrounding tissue. They were then loaded onto a calibrated, pre-heated (37° C.) wire myograph chamber (DMT Inc.) containing calcium-free phosphate buffered saline. Aortic samples were pre-stretched for 3 minutes to a 1-mm luminal diameter displacement that was returned to the non-stretched baseline, and this was repeated twice. To begin the experiment after pre-stretching, segments were stretched to a baseline force of 1 mN. Luminal displacement was increased incrementally (~10% increase) every 3 minutes, and the force was recorded following every 3-minute time period. Displacement was increased until mechanical failure of the tissue occurred, defined by an observed transient decrease in force. Stress and strain were calculated where stress was defined as: t=$\lambda$L/2HD. t=one-dimensional stress, $\lambda$=strain, L=one-dimensional load applied, H=wall thickness, D=length of vessel. Strain was defined as: $\lambda$=Ad/d(i). $\lambda$=strain, Ad=change in diameter, d(i)=initial diameter. The slope of the stress-strain curve was used to determine the elastic modulus as previously described (Fleenor B. S. et al. 2012b, Exp Gerontol. 47, 588-594).

Aortic Superoxide Production.

Measurement of superoxide production in the thoracic aorta was performed using electron paramagnetic resonance (EPR) spectroscopy, as previously described (LaRocca T. J. et al. 2013, Mech Ageing Dev. 134, 314-320). The aorta was removed and dissected free of perivascular fat and other surrounding tissue. 1-mm aortic segments were incubated for 1 hour at 37° C. in Krebs-Hepes buffer with the superoxide-specific spin probe 1-hydroxy-3methoxycarbonyl-2,2,5,5-tetramethylpyrrolidine (CMH; 0.5 mM; Enzo Life Sciences, Inc., Farmington, N.Y., USA) for detection of whole-cell superoxide production. The signal amplitude was analyzed using an MS300 X-band EPR spectrometer (Magnettech GmbH, Berlin, Germany) with the following settings: centrefield, 3350 G; sweep, 80 G; microwave modulation, 3000 mG, and microwave attenuation, 7 dB. Data are presented relative to the YC group mean.

Western Blotting.

Aortas were used as a surrogate large elastic artery to provide sufficient tissue for analysis of protein expression by Western blot as described previously (Donato A. J. et al. 2013, J Physiol. 589, 4545-4554; Gano L. B. et al. 2014, Am J Physiol Heart Circ Physiol. 307, H1754-1763). Aortas were excised, cleared of perivascular fat and other surrounding tissues, and frozen in liquid nitrogen before storage at −80° C. The tissue was homogenized in ice-cold Radioimmunoprecipitation Assay (RIPA) lysis buffer containing protease and phosphatase inhibitors [Protease Inhibitor Cocktail Tablet (Roche, Indianapolis, Ind., USA) and 0.01% phosphatase inhibitor cocktail (Sigma Aldrich Corp.)] and pulverized using a Bullet Blender. Protein was loaded on 4-12% polyacrylamide gels (12 µg per well), separated by electrophoresis, and transferred onto nitrocellulose membranes (Criterion System; Bio-Rad Laboratories, Inc., Hercules, Calif., USA) for Western blot analysis. Membranes were incubated with the following primary antibodies overnight at 4° C.: anti-nitrotyrosine (NT 1:500; Abcam, Cambridge, Mass., USA), anti-sirtuin1 (SIRT1 1:1000; Abcam), anti-p65 (subunit of nuclear factor kappa B (NFκB; 1:500 Cell Signaling Technology Inc., Danvers, Mass., USA)), and anti-acetylated p65 (subunit of nuclear factor kappa B [ac-NFκB; 1:500 Cell Signaling Technology Inc.]). Proteins were visualized on a digital acquisition system (ChemiDoc-It; UVP, Inc., Upland, Calif., USA) using chemiluminescence with horseradish peroxidase-conjugated secondary antibodies (Jackson ImmunoResearch Laboratories, Inc., Westgrove, Pa., USA), enhanced chemiluminescence (ECL) substrate (Pierce Biotechnology, Inc., Rockford, Ill., USA). Relative intensity was quantified using Image-J Software Version 1.0. All data were normalized to expression of alpha smooth muscle actin (a actin 1:5000; Abcam). The ratio of acetylated to total p65 was determined by running two identical Western blots. One membrane was probed for acetylated p65, while the other was probed for total p65. Each value was normalized to a actin in the corresponding gel. The ratio of acetylated to total p65 was determined for each animal and then normalized to the YC group mean.

Immunohistochemistry.

Immunohistochemistry was used to determine aortic expression of collagen type I and elastin as previously described (Fleenor B. S. et al. 2010 J Physiol. 588, 3971-3982). Thoracic aorta segments were excised and cleared of perivascular fat and other surrounding tissue. The segments were frozen in optimal cutting temperature compound (OCT; Fisher Scientific Inc., Waltham, Mass., USA) in liquid nitrogen-cooled isopentane. Aortic segments (7 μm each) were fixed in acetone for 10 minutes and washed in Tris Buffer. All slides were stained with the Dako EnVision™+ System-HRP-DAB-kit (Dako, Carpinteria, Calif.) according to the manufacturer's protocol using the following primary antibodies: collagen type I (Col1; 1:100, Millipore Corp., Temecula, Calif., USA) and alpha elastin (a elastin; 1:50, Abcam). Primary antibodies were incubated for 1 hour at 4° C. The labeled polymer was applied for 30 minutes and staining was visualized after a 4-minute exposure to diaminobenzidine (DAB). Slides were then dehydrated and cover-slipped. Digital photomicrographs were obtained using a Nikon Eclipse TS100 photomicroscope, and quantification was performed with Image-J Software Version 1.0. The adventitial and medial layers for each sample were quantified together for whole vessel expression. Slides from multiple batches were normalized to the same representative YC animal and normalized to the YC mean of each staining day.

Statistical Analyses.

Data are presented as mean±SEM in text, figures and tables. All analyses were performed with SPSS. A one-way ANOVA (Analysis of Variance) was used to analyze morphological characteristics, maximum EDD, NO-mediated EDD, EPR spectroscopy, aPWV, elastic modulus, Western blots, and immunohistochemistry. Within-group differences in the maximal EDD dose response to acetylcholine in the absence vs. presence of TEMPOL was determined using two-factor (group×treatment) repeated-measures ANOVA. When a significant main effect was observed, Tukey post-hoc tests were used to determine specific pairwise differences. Significance was set at $p<0.05$.

Results

Animal Characteristics and NMN Intake

Selected morphological characteristics are shown in Table 1.

TABLE 1

|  | YC | OC | YNMN | ONMN |
|---|---|---|---|---|
| Body mass (g) | 30.1 ± 0.7 | 30.3 ± 0.6 | 28.0 ± 0.9 | 30.8 ± 0.6 |
| Heart mass (mg) | 145 ± 6 | 176 ± 7 * | 139 ± 7 | 182 ± 8 * |
| Quad mass (mg) | 176 ± 5 | 151 ± 4 * | 185 ± 6 | 146 ± 6 * |
| Gastroc mass (mg) | 151 ± 3 | 124 ± 3 * | 148 ± 8 | 126 ± 2 * |
| WAT mass (mg) | 730 ± 65 | 472 ± 41 * | 600 ± 35 | 430 ± 50 * |
| SubQ fat mass (mg) | 334 ± 32 | 207 ± 17 * | 252 ± 16 | 201 ± 23 * |

Values are mean ± SEM
* $p < 0.05$ vs. YC.
n = 13-19/group.
Quad, quadriceps; Gastroc, gastrocnemius; WAT, white adipose tissue; SubQ, subcutaneous fat.

There were no significant differences in body mass across the four groups. An age-related increase in heart mass and a decrease in fat and muscle mass, which were not altered with NMN treatment, were observed. All animals consumed the same quantity of food throughout the duration of the study, and NMN intake was similar in both young and old treated groups.

NMN Treatment Restores Maximum EDD and NO-Mediated EDD in Old Mice

Baseline carotid artery diameters (μm) assessed ex vivo were greater in old mice (controls: 480±17; treated: 478±9) vs. young mice (controls: 424±4; treated: 432±5). NMN treatment had no significant effect on baseline carotid artery diameters. Maximum EDD to acetylcholine assessed ex vivo was lower in old control compared with young control mice and was mediated in part by a diminished nitric oxide (NO) dilatory influence, as indicated by a smaller reduction in EDD in the presence vs. absence of the NO synthase inhibitor N-G-nitro-L-arginine (L-NAME) (FIGS. 1A, 1B, n=13-22/group). NMN treatment rescued EDD in old mice by restoring NO-mediated dilation, but had no effect in young treated animals (FIGS. 1A, 1B). There were no significant differences in maximal EDD or NO-mediated EDD in young and old treated animals vs. young controls. Endothelium-independent dilation to the NO donor sodium nitroprusside, a control to assess vascular smooth muscle sensitivity to NO, was not significantly different among the groups (FIG. 1C, n=7-22/group). Values are mean±SEM. *$p<0.05$ vs. all.

NMN Reduces Vascular Oxidative Stress

Ex vivo incubation with the superoxide dismutase mimetic, 4-Hydroxy-2,2,6,6-tetramethylpiperidine-1-oxyl (TEMPOL), restored EDD in carotid arteries of old control animals, while having no significant effect in the other groups (FIG. 2A, n=5-9/group. * $p<0.05$ vs. TEMPOL), indicating excessive superoxide-mediated endothelial dysfunction with aging. To further assess the influence of aging and NMN treatment on oxidative stress in arteries, aortas were used because of the greater amount of tissue provided for biochemical assay. Compared with young mice, aortas from old animals exhibited increased superoxide production, directly assessed by electron paramagnetic resonance spectroscopy (FIG. 2B; values are normalized to YC mean value, representative EPR signal below, n=4-9/group), and increased nitrotyrosine abundance (FIG. 2C), a marker of oxidative protein modification and cellular footprint of oxidative stress. NMN treatment ameliorated the age-related increase in superoxide production (FIG. 2B) and markedly reduced aortic nitrotyrosine abundance in old mice (FIG. 2C, n=4-6/group), while having no significant effect in young mice. Data are expressed relative to α-smooth muscle actin and normalized to YC mean value. Values are mean±SEM. * $p<0.05$ vs. all; # $p<0.05$ vs. YC. Together, these data indicate that NMN reverses age-associated oxidative stress in arteries, which, in turn, mediates improvements in endothelial function.

NMN Treatment Normalizes Aortic Stiffness in Old Mice

Figure 3A:
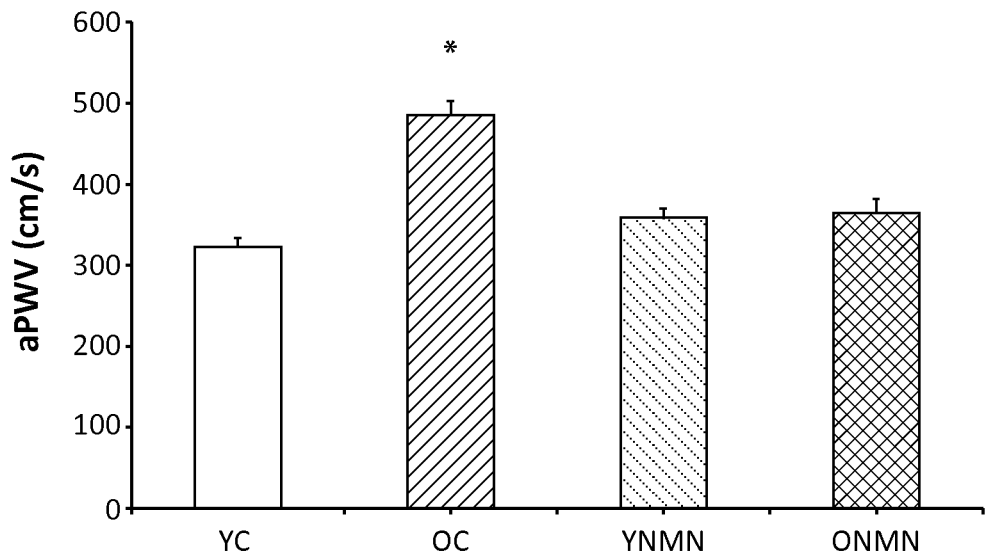
FIG. 3 illustrates aortic pulse wave velocity (aPWV) in young and old control (YC and OC) and young and old NMN-treated (YNMN and ONMN) mice (FIG. 3A); elastic modulus (FIG. 3B); total arterial collagen-I (Col1) expression in aorta (FIG. 3C); and total elastin expression in aorta (FIG. 3D).
Figure 3B:
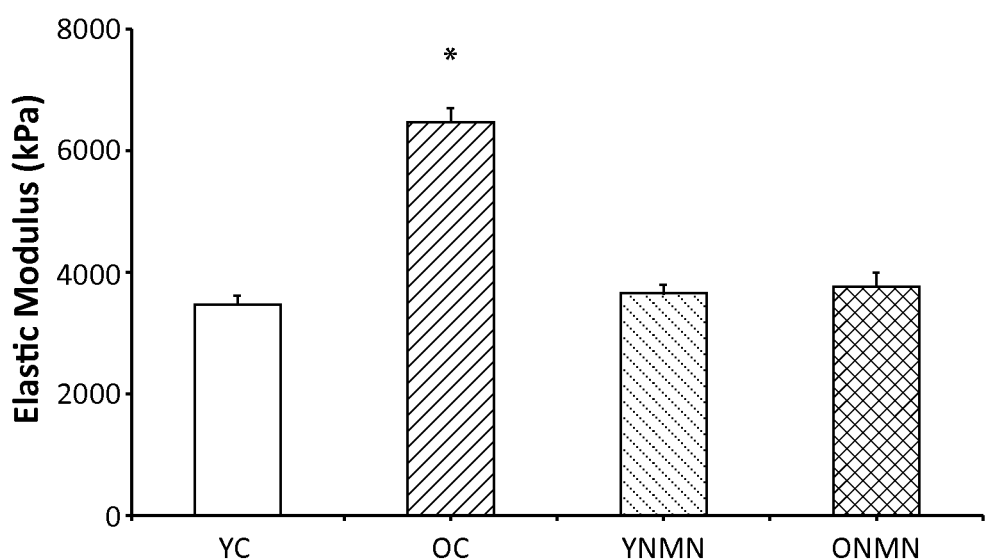

Large elastic artery stiffness, as assessed in vivo by aPWV, was greater in old control compared to young control mice (FIG. 3A, n=5-9/group). NMN treatment reversed the age-associated increase in aPWV in old mice, while having no significant effect in young mice (FIG. 3A). Similarly, the elastic modulus, an in vitro index of intrinsic arterial stiffness, was higher in old controls compared to young and was normalized with NMN treatment (FIG. 3B, n=5-6/group). Thoracic aortas from old control animals exhibited markedly increased collagen type I expression (FIG. 3C, n=4-9/group) and diminished elastin (FIG. 3D) compared to young controls. In old mice, NMN reduced arterial collagen type I to levels of young mice (FIG. 3C), and increased elastin to levels not significantly different from young mice (FIG. 3D, n=4-11/group). Values normalized to YC mean value. Values are mean±SEM. Bars=100 µm. * $p<0.05$ vs. all; # $p<0.05$ vs. YC.

NMN Treatment Activates SIRT1

Figure 4A:
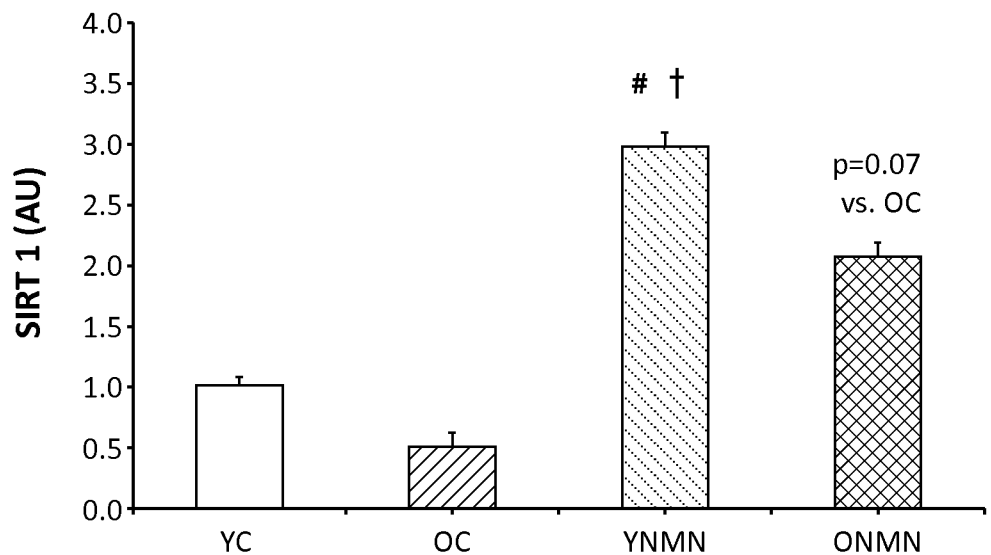
FIG. 4 illustrates SIRT1 expression in aorta of young and old control (YC and OC) and young and old NMN-treated (YNMN and ONMN) mice (FIG. 4A) and ratio of acetylated to total NFκB in aorta (FIG. 4B).
Figure 4B:
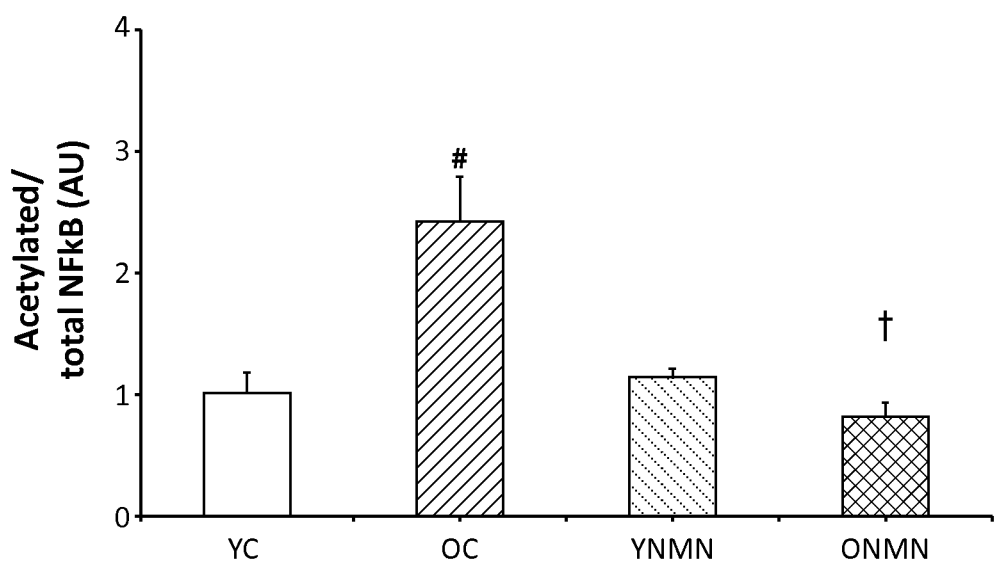

Mean levels of aortic SIRT1 expression were ~50% lower in the old animals, compared to young mice, although the difference did not reach statistical significance (FIG. 4A, n=5-7/group). NMN treatment increased SIRT1 protein expression in young animals and tended to increase SIRT1 in old animals (FIG. 4A). SIRT1 activation was determined by assessing the ratio of acetylated to total NFκB (p65 subunit) (FIG. 4B). This ratio was markedly higher in aorta of old control animals compared to young controls ($p<0.05$), indicating that aortic SIRT1 activity was reduced with aging. Data are expressed relative to α-smooth muscle actin and normalized to YC mean value. Values are mean±SEM, # $p<0.05$ vs. YC; † $p<0.05$ vs. OC. NMN treatment restored aortic SIRT1 activity in old animals ($p<0.05$; FIG. 4B, n=5-11/group).

The data demonstrates that 8 weeks of NMN treatment restored arterial SIRT1 activity and ameliorated age-associated endothelial dysfunction and large elastic artery stiffening in male C57Bl/6 mice. These improvements were associated with restored NO bioavailability, reduced oxidative stress, and complete or partial normalization of structural proteins in the arterial wall.

NMN Improves NO-Mediated EDD and Reduces Arterial Oxidative Stress

Endothelial dysfunction is the major antecedent to atherosclerosis, a predictor of clinical CVD risk, and is linked to many common disorders of aging including cognitive impairments, Alzheimer's Disease, motor dysfunction, insulin resistance and sarcopenia (Heitzer T. et al. 2001, Circulation. 104, 2673-2678; Gokce N. et al. 2002, Circulation. 105, 1567-1572; Widlansky M. E. et al. 2003, J Am Coll Cardiol. 42, 1149-1160; Seals D. R. et al. 2011, Clin Sci 120, 357-375; Seals D. R. et al. 2014, Physiology (Bethesda). 29, 250-264). Motor and cognitive functions are associated with the maintenance of independence and quality of life in older adults and represent clinical endpoints. A reversal of age-associated endothelial dysfunction by oral NMN treatment was demonstrated. Aging in the control animals was associated with an impairment in ex vivo carotid artery EDD in response to acetylcholine due to reduced NO-mediated dilation (FIGS. 1A-1B). The latter was determined as the difference in EDD in the absence vs. presence of NO production achieved by co-administration of the NO synthase inhibitor, NG-nitro-L-arginine methyl ester (L-NAME) (Max Dilation$_{ACh}$–Max Dilation$_{ACh+L-NAME}$; n=5-12/group). NMN treatment substantially or completely restored EDD by restoring NO-mediated dilation. The improvement in EDD with NMN treatment in old mice is not believed to be due to an increase in vascular smooth muscle sensitivity to NO because NMN did not influence dilation in response to administration of a NO donor (sodium nitroprusside), i.e., a dilation that is not induced by endothelial NO production.

The results demonstrate that the effects of aging and NMN treatment on endothelial function were mediated by differences in oxidative stress. Pharmaco-functional experiments revealed that arteries from old untreated mice showed restoration of maximal EDD in the presence of the superoxide dismutase mimetic, TEMPOL, indicating that excessive superoxide-related oxidative stress may be the cause of the age-associated impairment of EDD (FIG. 2A). In contrast to the untreated old mice, TEMPOL caused no significant improvement in EDD in old mice receiving NMN treatment. NMN treatment may restore EDD in the old animals by abolishing superoxide-mediated suppression of endothelial function with aging.

Figure 2B:
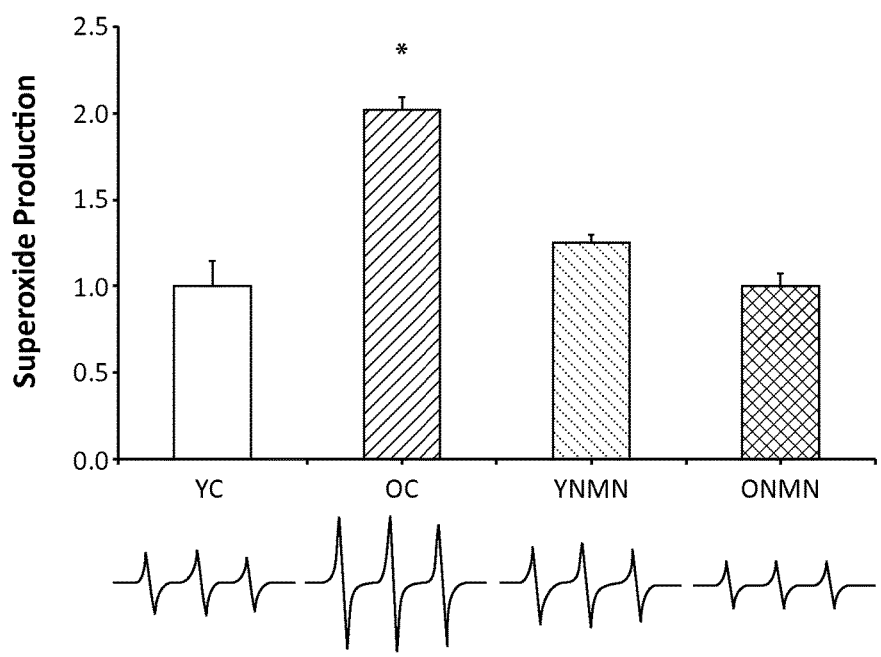
Figure 2C:
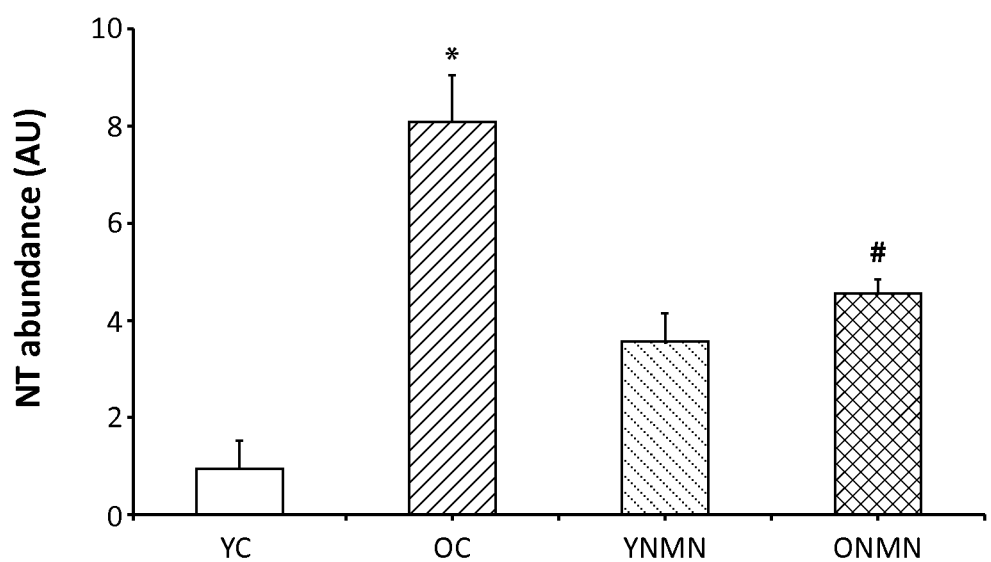

These function-based observations are supported by direct assessments of arterial superoxide production using electron paramagnetic resonance spectroscopy, as well as results for nitrotyrosine, a cellular marker of oxidative stress. Aging in control animals was associated with marked increases in both aortic superoxide production and nitrotyrosine abundance (FIGS. 2B-2C). In response to NMN treatment, a normalization of aortic superoxide production and a marked reduction in nitrotyrosine abundance in old mice was observed.

Collectively, these findings support the various aspects and embodiments of the invention comprising prevention of age-related decline, prevention of stress with treatment of NMN, that oxidative stress is a key contributor to age-associated endothelial dysfunction and that the suppression of oxidative stress may be a major mechanism by which NMN exerts its beneficial effects on endothelial function in old animals.

NMN Reduces Large Elastic Artery Stiffness

NMN treatment reverses the age-associated increase in two functional indices of aortic stiffness: aPWV, the gold standard clinical measure of large elastic artery stiffness, and the elastic modulus, an in vitro measure of the intrinsic mechanical properties of arteries (FIGS. 3A-3B).

Figure 3C:
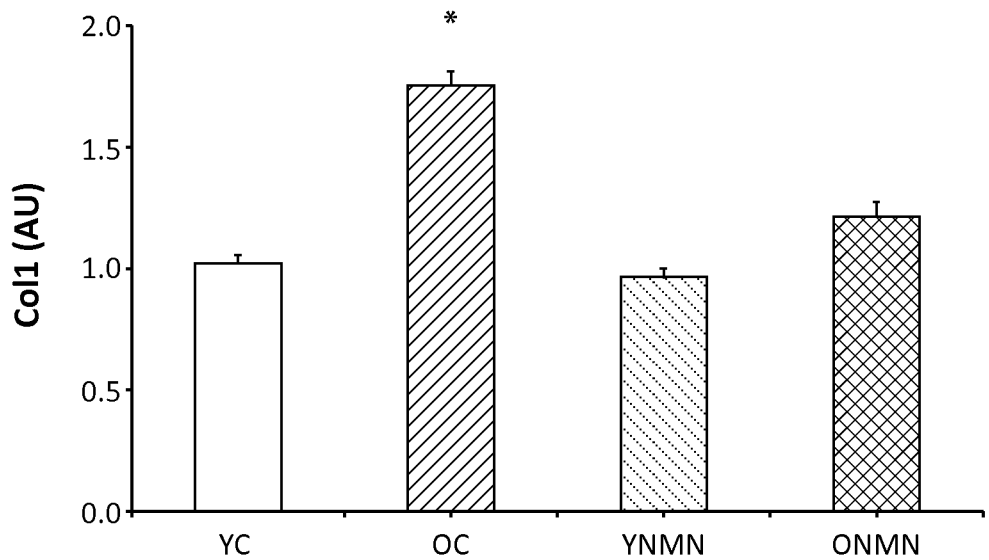
Figure 3D:
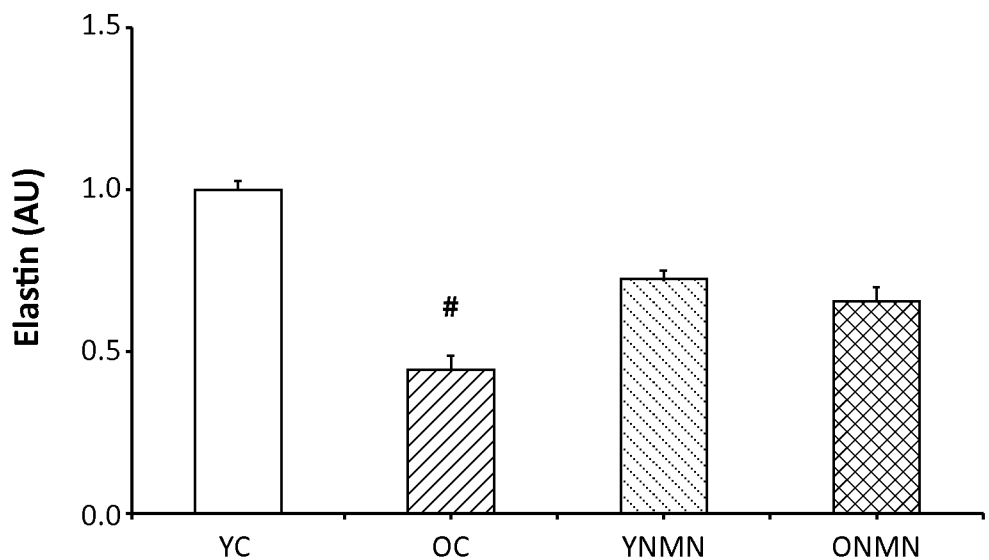

NMN treatment reverses the accumulation of whole-vessel collagen type I and enhances arterial elastin in old mice (FIGS. 3C-3D). NMN reduces arterial stiffness, at least in part, by ameliorating the structural changes that occur to arteries with advancing age.

Reductions in aortic collagen in old mice subjected to other short-term late-life behavioral or pharmacological interventions has been observed. NMN also induced a partial restoration of aortic elastin to levels not significantly different from young control animals. An increase in aortic elastin with any other late-life lifestyle or pharmacological intervention in mice has not been observed, although life-long CR protects against the loss of elastic properties within the arteries, including elastin degradation (Fornieri C. et al. 1999, Connect Tissue Res. 40, 131-143). These results demonstrate that NMN partially restores arterial elastin.

Activation of SIRT1 by NMN

NAD$^+$ measurements in the aortic samples could not be acquired with confidence, likely due to the limited amount of tissue and the time needed to extract the aorta compared with larger, more easily obtained tissues such as skeletal muscle or white adipose tissue. Treatment with NMN selectively restored the activity of SIRT1 in the arteries of old mice to that of young controls, as indicated by a decrease in the ratio of acetylated to total p65 subunit of the transcription factor NFκB (FIG. 4B).

All references cited herein are hereby incorporated by reference in their entirety.

It is believed that the disclosure set forth above encompasses at least one distinct invention with independent utility. While the invention has been disclosed in the exemplary forms, the specific embodiments thereof as disclosed and illustrated herein are not to be considered in a limiting sense as numerous variations are possible. Equivalent changes, modifications and variations of various embodiments, materials, compositions and methods may be made within the scope of the present invention, with substantially similar results. The subject matter of the inventions includes all novel and non-obvious combinations and subcombinations of the various elements, features, functions and/or properties disclosed herein.

Benefits, other advantages, and solutions to problems have been described herein with regard to specific embodiments. However, the benefits, advantages, solutions to problems, and any element or combination of elements that may cause any benefit, advantage, or solution to occur or become more pronounced are not to be construed as critical, required, or essential features or elements of any or all the claims of the invention. Many changes and modifications within the scope of the instant invention includes all such modifications. Corresponding structures, materials, acts, and equivalents of all elements in the claims below are intended to include any structure, material, or acts performing the functions in combination with other claim elements as specifically claimed. The scope of the invention should be determined by the appended claims and their legal equivalents, rather than by the examples given above.

The invention claimed is:

1. A method for treatment of vascular endothelial dysfunction, comprising:
   determining an indicator of vascular endothelial dysfunction in a subject, wherein the indicator is selected from a group consisting of: endothelium-dependent dilation; artery stiffness; and aortic pulse wave velocity; and
   administering a daily dose of a composition comprising nicotinamide mononucleotide and a pharmaceutical excipient, wherein the composition comprises from about 1 mg to about 25 mg of nicotinamide mononucleotide per kg body weight per day and wherein the composition is administered chronically to said subject in response to the indicator.

2. The method of claim 1, further comprising determining a subsequent effect on vascular endothelial dysfunction in the subject.

3. The method of claim 1, wherein the endothelium-dependent dilation is associated with increased superoxide production.

4. The method of claim 1, wherein the endothelium-dependent dilation is associated with decreased SIRT1 expression.

5. The method of claim 1, wherein extent of endothelium-dependent dilation and/or artery stiffness is decreased in response to administration of the composition comprising nicotinamide mononucleotide.

6. The method of claim 5, wherein the decrease in the extent of endothelium-dependent dilation further comprises a decrease in superoxide production and an increase in nitric oxide bioavailability.

7. The method of claim 5, wherein the decrease in the extent of endothelium-dependent dilation further comprises an increase in SIRT1 protein expression and activity.

8. The method of claim 1, wherein the composition is administered over a period of time of about 30 days, about 3 months, about 6 months, about 12 months, about 18 months, about 2 years, about 5 years, about 7 years, about 10 years, about 15 years, about 20 years, about 25 years, about 30 years, about 35 years, about 40 years, or continued therapy over the lifetime of the subject.

9. The method of claim 1, wherein the composition comprises about 18 mg of nicotinamide mononucleotide per kg body weight per day.

10. A method of decreasing the extent of endothelium-dependent dilation and/or arterial stiffness in a subject, comprising:
    determining the extent of endothelium-dependent dilation and/or arterial stiffness in a subject, wherein the indicator is selected from a group consisting of: endothelium-dependent dilation; artery stiffness; and aortic pulse wave velocity; and
    administering a daily dose of a composition comprising nicotinamide mononucleotide and a pharmaceutical excipient wherein the composition comprises from about 1 mg to about 25 mg of nicotinamide mononucleotide per kg body weight per day and wherein the composition is administered chronically to said subject.

11. The method of claim 10, wherein a decrease in the extent of endothelium-dependent dilation and/or arterial stiffness is associated with an increase in bioavailability of nicotinamide adenine dinucleotide (NAD+).

12. The method of claim 11, wherein a decrease in the extent of endothelium-dependent dilation and/or arterial stiffness further comprises a decrease in superoxide production, an increase in bioavailability of nitric oxide, and/or an increase in SIRT1 protein expression and activity.

13. The method of claim 10, wherein the composition comprises about 18 mg of nicotinamide mononucleotide per kg body weight per day.

14. A method for modulating endothelium-dependent dilation and/or arterial stiffness in a subject, comprising:
    administering a daily dose of a composition comprising nicotinamide mononucleotide and a pharmaceutical excipient wherein the composition comprises from about 1 mg to about 25 mg of nicotinamide mononucleotide per kg body weight per day and wherein the composition is administered chronically to said subject.

15. The method of claim 14, wherein the extent of endothelium-dependent dilation is associated with increased superoxide production.

16. The method of claim 14, wherein the extent of endothelium-dependent dilation is associated with decreased SIRT1 expression.

17. The method of claim 14, wherein the extent of endothelium-dependent dilation and/or artery stiffness is decreased in response to administration of the composition comprising nicotinamide mononucleotide.

18. The method of claim 14, wherein the extent of endothelium-dependent dilation further comprises a decrease in superoxide production and an increase in nitric oxide bioavailability.

19. The method of claim 14, wherein the extent of endothelium-dependent dilation further comprises an increase in SIRT1 protein expression and activity.

20. The method of claim 14, wherein the composition is administered over a period of time of about 30 days, about 3 months, about 6 months, about 12 months, about 18 months, about 2 years, about 5 years, about 7 years, about 10 years, about 15 years, about 20 years, about 25 years, about 30 years, about 35 years, about 40 years, or continued therapy over the lifetime of the subject.

21. The method of claim 14, wherein the composition comprises about 18 mg of nicotinamide mononucleotide per kg body weight per day.

\* \* \* \* \*